United States Patent
Adahan

(10) Patent No.: US 8,303,276 B2
(45) Date of Patent: Nov. 6, 2012

(54) PUMP AND EXHALATION VALVE CONTROL FOR RESPIRATOR APPARATUS

(75) Inventor: Carmeli Adahan, Jerusalem (IL)

(73) Assignee: Covidien LP, Mansfield, MA (US)

( * ) Notice: Subject to any disclaimer, the term of this patent is extended or adjusted under 35 U.S.C. 154(b) by 998 days.

(21) Appl. No.: 12/314,431

(22) Filed: Dec. 10, 2008

(65) Prior Publication Data

US 2010/0139660 A1    Jun. 10, 2010

(51) Int. Cl.
*F04B 39/10* (2006.01)
*F04B 35/04* (2006.01)
*A62B 7/04* (2006.01)

(52) U.S. Cl. ............ 417/534; 417/415; 128/204.26

(58) Field of Classification Search .......... 417/534, 417/441, 415, 410.1, 521, 569; 128/205.24, 128/204.18, 204.26
See application file for complete search history.

(56) References Cited

U.S. PATENT DOCUMENTS

| | | | | |
|---|---|---|---|---|
| 3,264,392 A * | 8/1966 | Taplin | ............. | 264/231 |
| 3,358,680 A * | 12/1967 | Chabanier | ............. | 128/204.29 |
| 3,375,759 A * | 4/1968 | Smith | ............. | 92/98 D |
| 3,714,941 A * | 2/1973 | Kipling | ............. | 128/205.24 |
| 3,918,447 A * | 11/1975 | Inkster et al. | ............. | 128/205.18 |
| 3,932,066 A * | 1/1976 | Eyrick et al. | ............. | 417/328 |
| 4,459,982 A * | 7/1984 | Fry | ............. | 128/204.23 |
| 4,726,745 A * | 2/1988 | Adahan | ............. | 417/413.1 |
| 4,773,305 A * | 9/1988 | Nissels | ............. | 92/98 D |
| 4,774,874 A * | 10/1988 | Adahan | ............. | 92/59 |
| 4,807,616 A | 2/1989 | Adahan | | |
| 4,823,787 A | 4/1989 | Adahan | | |
| 4,836,198 A * | 6/1989 | Gates | ............. | 128/205.18 |
| 4,941,469 A * | 7/1990 | Adahan | ............. | 128/205.18 |
| 5,063,925 A | 11/1991 | Frank et al. | | |
| 5,092,326 A * | 3/1992 | Winn et al. | ............. | 128/205.13 |
| 5,484,270 A * | 1/1996 | Adahan | ............. | 417/415 |
| 5,683,232 A * | 11/1997 | Adahan | ............. | 417/440 |
| 5,762,480 A | 6/1998 | Adahan | | |
| 5,881,722 A * | 3/1999 | DeVries et al. | ............. | 128/204.21 |
| 6,073,630 A * | 6/2000 | Adahan | ............. | 128/205.24 |
| 6,247,472 B1 * | 6/2001 | Moseley | ............. | 128/205.26 |
| 6,283,122 B1 * | 9/2001 | Adahan | ............. | 128/205.24 |
| 6,302,105 B1 * | 10/2001 | Wickham et al. | ............. | 128/204.18 |
| 2002/0057972 A1 * | 5/2002 | Barinaga et al. | ............. | 417/413.3 |

OTHER PUBLICATIONS

International Search Report and Written Opinion for PCT/US2009/058060 dated Mar. 29, 2010.

* cited by examiner

*Primary Examiner* — Charles Freay
*Assistant Examiner* — Alexander Comley
(74) *Attorney, Agent, or Firm* — Procopio, Cory, Hargreaves & Savitch LLP

(57) ABSTRACT

Double acting respiratory pump apparatus including a pump member reciprocable with respect to two pump chambers to deliver air to a patient via a respirator exhalation system, which also facilitates exhalation of the patient. The exhalation system has a pump unit that is operatively connected to an exhalation valve member and configured for selectively generating an air pressure sufficient for pressurizing one side of the valve member for closing the same when said exhalation system is operating in inhalation mode, and may be operated for opening to allow the patient to exhale therethrough.

23 Claims, 2 Drawing Sheets

PUMP AND EXHALATION VALVE CONTROL FOR RESPIRATOR APPARATUS

FIELD OF THE INVENTION

The present invention relates to pumps, and particularly to pumps useful in respirator or ventilator apparatus. The invention also relates to an exhalation valve assembly useful in such pumps and respirator or ventilator apparatus.

BACKGROUND OF THE INVENTION

Respirator apparatus, sometimes called ventilator apparatus and interchangeably referred to thus herein, is widely used for administering artificial respiration or ventilatory assistance to a patient.

By way of general background, the following US patents disclose examples of such an apparatus, or of a pump and/or exhalation valve useful in such apparatus.

U.S. Pat. Nos. 4,807,616, 4,823,787 and 4,941,469 disclose a ventilator apparatus comprising a pump; a delivery conduit for delivering pressurized air to a patient; a relief valve preventing the pressure in the delivery conduit from rising above a predetermined peak value; a sensor for sensing the pressure in the delivery conduit; a storage device for storing the sensed peak pressure; and a comparator for continuously comparing the sensed pressure with the stored peak pressure and effective to energize the pump whenever the sensed pressure is below the stored peak pressure, and to deenergize the pump whenever the sensed pressure is generally equal to the stored peak pressure.

U.S. Pat. Nos. 6,073,630, 5,484,270 and 5,683,232 disclose a reciprocating pump particularly useful in ventilator apparatus, and includes a piston reciprocatable axially within a cylinder and dividing its interior into an inlet chamber and an outlet chamber, a wall fixed within the inlet chamber, and a drive housing fixed to the wall. The drive housing includes a motor, a rotor rotatable by the motor, a nut rotatable within the drive housing, and a screw threadedly coupled at one end to the nut and fixed at its opposite end to the piston. The piston is substantially unrestrained for axial and rotary movement such that forward and reverse rotation of the nut by the motor reciprocates the screw and the piston axially of the cylinder, and also permits the screw and the piston to rotate with respect to the cylinder to thereby even out wear between the piston and cylinder.

U.S. Pat. No. 6,283,122 discloses an exhalation assembly which includes a hollow flow-through body, having an air inlet port and an air outlet port. The inlet port is arranged to receive air for supplying to a patient, and the air outlet port is arranged to provide air to a patient. The device also includes an exhalation valve connected to the flow-through body, for facilitating selectable exhalation by a patient to whom air is being supplied. The exhalation valve includes an air exhalation port arranged to permit therethrough an outflow of exhaled air and a valve member arranged to selectably cover the exhalation port in response to a closure pressure applied thereto, and to uncover the exhalation port in response to an exhalation pressure applied thereto from the flow-through body through the exhalation port Also included is a pressure source for selectably applying a closure pressure to the valve member, wherein the valve member is operative to cover the exhalation port in response to at least a minimum closure pressure which has a smaller magnitude than an opposing exhalation pressure Further by way of general background, U.S. Pat. No. 5,762,480 discloses a reciprocating machine that converts linear motion to rotary motion or vice-versa and is associated with a supply of working fluid, and includes rotational power apparatus having a rotational motion transfer member; a cylinder defining a longitudinal axis and having a first end at which are located working fluid input and output apparatus, and further having a second end; a piston located within the cylinder and arranged for linear, reciprocating travel along the longitudinal axis between the first and second ends; a connecting rod having a first end connected to the piston, and further having a second end portion; and linkage apparatus.

SUMMARY OF THE INVENTION

According to one aspect of the present invention, there is provided a pump apparatus, particularly useful for a respirator apparatus, the pump apparatus being a double acting respirator pump apparatus comprising a housing defining two pump chambers and a pump member reciprocable with respect to said pump chambers and configured to provide an inlet stroke and an outlet stroke with respect to each said chamber in each reciprocation cycle of said pump member, wherein said inlet stroke and said outlet stroke for each pump chamber defines for the respective pump chamber a displacement volume that is displaced in the respective pump chamber by reciprocation of the pump member in one reciprocation cycle between the respective inlet stroke and the respective outlet stroke, and wherein a volume of at least one said pump chamber at the end of the respective said output stroke thereof is a first proportion of the respective said displacement volume, wherein said first proportion is not less than about 50%, and wherein said pump member comprises a piston reciprocably mounted with respect to said pump chambers via a rolling convolution diaphragm peripherally joined to the piston and anchored with respect to each said pump chamber, and wherein said diaphragm is configured for avoiding being collapsed or reversed during the output stroke of each said pump chamber.

The pump apparatus according to this aspect of the invention may comprise one or more of the following features A to K, in any desired combination:

(A) The diaphragm may be configured to have a portion thereof that bulges in a direction towards one said pump chamber and away from the other said pump chamber regardless of a position or direction of travel of said piston within said reciprocation cycle during operation of said pump.

(B) The pump comprises a pump inlet port and a pump outlet port, wherein said pump inlet port is in fluid communication with an inlet valve of at least one pump chamber via at least one inlet chamber having a first volume, and wherein said pump outlet port is in fluid communication with an outlet valve of at least one pump chamber via at least one outlet chamber having a second volume, and wherein each one of said first volume and said second volume is at least about 50% of said displacement volume of said respective pump chamber.

(C) Referring to feature (B), each said pump chamber may comprise a respective said inlet chamber and a respective said outlet chamber, and wherein said outlet chamber of one said chamber is in fluid communication with said outlet chamber of the other said pump chamber, and wherein said inlet chamber of one said chamber is in fluid communication with said inlet chamber of the other said pump chamber.

(D) The diaphragm may have a convolution diameter, i.e., a projected dimension along a first direction substantially orthogonal to a reciprocation direction of said piston, that is between about 5% and about 15% of a diameter of said piston.

(E) Regarding feature (D), the diaphragm may be made, for example, from a flexible material, having a hardness of between about 50 Shore A and about 70 Shore A. For example, such a flexible material may be a rubber-based compound.

(F) The piston may have an axial displacement in a reciprocation direction of said piston between a top dead center position corresponding to an end of an output stroke of one said pump chamber, and a bottom dead center position corresponding to an end of an output stroke of the other said pump chamber, wherein said axial displacement or translation that is between about 10% and about 20% of a diameter of said piston as projected in a direction substantially orthogonal to said reciprocation direction.

(G) The piston is driven by a motor by means of a crank and piston shaft arrangement.

(H) Regarding feature (G), the crank and piston shaft arrangement may be accommodated in a shaft housing in fluid communication with one said pump chamber, and wherein said motor is accommodated in a motor housing and operatively connected to said crank in a manner providing for sealing of said respective pump chamber within respect to said motor housing.

(I) Regarding feature (H), the motor may comprise a driveshaft operatively connected to said crank, and said driveshaft is mounted with respect to said shaft housing via a bearing arrangement, wherein said bearing arrangement comprises a seal for sealing said respective pump chamber within respect to said motor housing. Such a seal may be an integral seal, i.e., integral to the motor shaft bearing.

(J) Regarding at least feature (C), the housing may comprise a first end part including said inlet chamber and said outlet chamber of one said pump chamber, a second end part including said inlet chamber and said outlet chamber of the other said pump chamber, a first cylinder part and a second cylinder part, wherein said diaphragm is anchored between said first cylinder part and said second cylinder part to define one said pump chamber in each one of said first cylinder part and said second cylinder part, and wherein said first end part and said second end part are respectively mountable to said first cylinder part and said second cylinder part.

(K) Regarding at least feature (C), the apparatus comprises a pump inlet port and a pump outlet port, wherein said pump inlet port is in fluid communication with said inlet chamber of each said pump chamber, and wherein said pump outlet port is in fluid communication with said outlet chamber of each said pump chamber.

It is to be noted that feature (J) is considered per se novel, and applicable mutatis mutandis to other types and configurations of pumps.

It is also to be noted that feature (I) is considered per se novel, and applicable mutatis mutandis to other types and configurations of pumps.

According to another broad aspect of the present invention, there is provided a pump apparatus, particularly useful for a respirator apparatus, the pump apparatus being a double acting respirator pump apparatus comprising a housing defining two pump chambers and a pump member reciprocable with respect to said pump chambers and configured to provide an inlet stroke and an outlet stroke with respect to each said chamber in each reciprocation cycle of said pump member, wherein said inlet stroke and said outlet stroke for each pump chamber defines for the respective pump chamber a displacement volume that is displaced though the respective pump chamber by reciprocation of the pump member in one reciprocation cycle between the respective inlet stroke and the respective outlet stroke, and wherein a volume of at least one said pump chamber at the end of the respective said output stroke thereof is not less than about 50% of said displacement volume, and wherein said pump member comprises a piston reciprocably mounted with respect to said pump chambers, wherein said piston has a axial displacement or translation in a reciprocation direction of said piston between a top dead center position corresponding to an end of an output stroke of one said pump chamber, and a bottom dead center position corresponding to an end of an output stroke of the other said pump chamber, wherein said axial translation is between about 10% and about 20% of a diameter of said piston as projected in a direction substantially orthogonal to said reciprocation direction.

The pump apparatus according to this aspect of the invention may comprise one or more of the features B, C, and F to K listed above, in any desired combination.

According to a broad aspect of the present invention, there is provided a pump apparatus, particularly useful for a respirator apparatus, the pump apparatus comprising a housing defining a two pump chambers and a piston reciprocable with respect to said pump chambers and configured to provide an inlet stroke and an outlet stroke with respect to each said chamber in each reciprocation cycle of said piston, wherein said piston is reciprocably mounted to said housing via a rolling convolution diaphragm peripherally joined to said piston and anchored with respect to each said chamber.

The pump apparatus according to this aspect of the invention may comprise one or more of the features A to K listed above, in any desired combination.

According to another broad aspect of the present invention, there is provided a pump apparatus, particularly useful for a respirator apparatus, the pump apparatus comprising a housing defining a two pump chambers and a pump member reciprocable with respect to said pump chambers and configured to provide an inlet stroke and an outlet stroke with respect to each said chamber in each reciprocation cycle of said piston, wherein said housing comprises a first end part including said inlet chamber and said outlet chamber of one said pump chamber, a second end part including said inlet chamber and said outlet chamber of the other said pump chamber, a first cylinder part and a second cylinder part, wherein said pump member is mounted for reciprocation with respect to said first cylinder part and said second cylinder part to define one said pump chamber in each one of said first cylinder part and said second cylinder part, and wherein said first end part and said second end part are respectively mountable to said first cylinder part and said second cylinder part.

For example, the pump member may comprise a piston that is reciprocably mounted to said housing via a rolling convolution diaphragm peripherally joined to said piston and anchored with respect to each said chamber, wherein said diaphragm is anchored between said first cylinder part and said second cylinder part.

The pump apparatus according to this aspect of the invention may comprise one or more of the features A to K listed above, in any desired combination, as appropriate.

At least some embodiments of the pump apparatus according to at least one of the above aspects of the invention provides one or more features, including inter alia, noise reduction, easy assembly, disassembly and replacement of parts.

According to another broad aspect of the invention there is provided a respirator exhalation system for facilitating exhalation of a patient connected to a respiratory apparatus, comprising an exhalation valve and a pump unit that is operatively connected to said exhalation valve and configured for selectively generating an air pressure sufficient for pressurizing one side of said valve member for closing the same when said exhalation system is operating in inhalation mode.

The respirator exhalation system comprises an exhalation valve assembly comprising a delivery tube comprising an inlet port for connection to a respiratory pump apparatus, an outlet port for connection to a patient, an exhalation valve discharge port leading to the atmosphere, and the valve member for alternately connecting the outlet port to one or another of said inlet port and said exhalation port, under the action of the respirator exhalation system.

The pump unit may comprise a pump control member and a housing having a seat, wherein a pumping chamber is defined between said pump control member and said seat, wherein in operation of said pump unit said pumping chamber comprises a confined volume of compressible air, and wherein said pumping chamber is in fluid communication with a control chamber comprising said valve member, and wherein said pump unit is configured for selectively bringing said pump control member into proximity with said housing seat to compress said volume of compressible air and thereby to generate a pump pressure for pressurizing said side of said valve member.

The pump control member may comprise an armature, and said housing may comprise an electric coil, and wherein operation of the pump unit energizes said coil and magnetically attracts said armature to bring said pump control member into proximity with said housing seat, thereby compressing air enclosed in said pumping chamber and generating said pump pressure.

The armature is connected to said housing seat via a flexible resilient diaphragm, wherein said diaphragm is configured for providing substantially hysteresis-free operation of said pump unit.

The diaphragm may extend between the armature and the housing seat, preventing contact therebetween when the coil is fully energized and providing for rapid separation therebetween when said coil is not energized, i.e., as soon as the coil stops being energized.

The diaphragm may be biased to space the armature away from the housing seat when the coil is not energized.

The pump unit may be configured for modulating the pump pressure by selectively variably energizing the coil. For example, the pump control member may be modulated to relieve the pressure acting on said side of the valve member of said exhalation valve at any desired pre-set pressure.

The respirator system may further comprise a two-way control valve in fluid communication with said pumping chamber and said side of said valve member, and configured for selectively venting said side of said valve member.

According to another broad aspect of the invention, there is provided a respiratory apparatus comprising the respiratory pump according to other aspects of the invention as defined herein, operatively connected to a respirator exhalation system for facilitating exhalation of a patient connected to said respiratory apparatus.

According to yet another broad aspect of the invention, there is provided a respiratory apparatus comprising a respiratory pump apparatus for delivering pressurized gas to a patient connected to said respiratory apparatus, the respiratory pump apparatus being operatively connected to a respirator exhalation system, according to aspects of the invention as defined herein.

At least some embodiments of the respirator system of the present invention have one or more of the following features.

The pump unit enables the valve member to be closed quickly, during the inhalation cycle, independently of the action of the respirator pump apparatus, and thus minimizes escape of air through the respirator exhalation system when the pump apparatus begins the inhalation cycle. This enables the pump apparatus to deliver a volume of air to the patient as required, and minimizes leaks which could otherwise be significant, particularly when delivering small amounts of air or when inhalation breaths are delivered at high frequency, for example to babies.

The provision of a two-way control valve increases the reliability of the respirator exhalation system, and avoids failures of equipment. In a respirator the failure of a valve to allow exhalation will result in suffocation of the patient, accordingly two valves perform the release of the exhalation valve simultaneously such that failure of one will not prevent exhalation.

At least some embodiments of the invention are directed to a double acting respirator pump apparatus including a pump member reciprocable with respect to two pump chambers to deliver air to a patient via a respirator exhalation system, which also facilitates exhalation of the patient. The exhalation system has a pump unit that is operatively connected to an exhalation valve member and configured for selectively generating an air pressure sufficient for pressurizing one side of the valve member for closing the same when said exhalation system is operating in inhalation mode, and may be operated for opening to allow the patient to exhale therethrough.

BRIEF DESCRIPTION OF THE DRAWINGS

In order to understand the invention and to see how it may be carried out in practice, embodiments will now be described, by way of non-limiting example only, with reference to the accompanying drawings, in which.

DETAILED DESCRIPTION OF EMBODIMENTS

Figure 1:
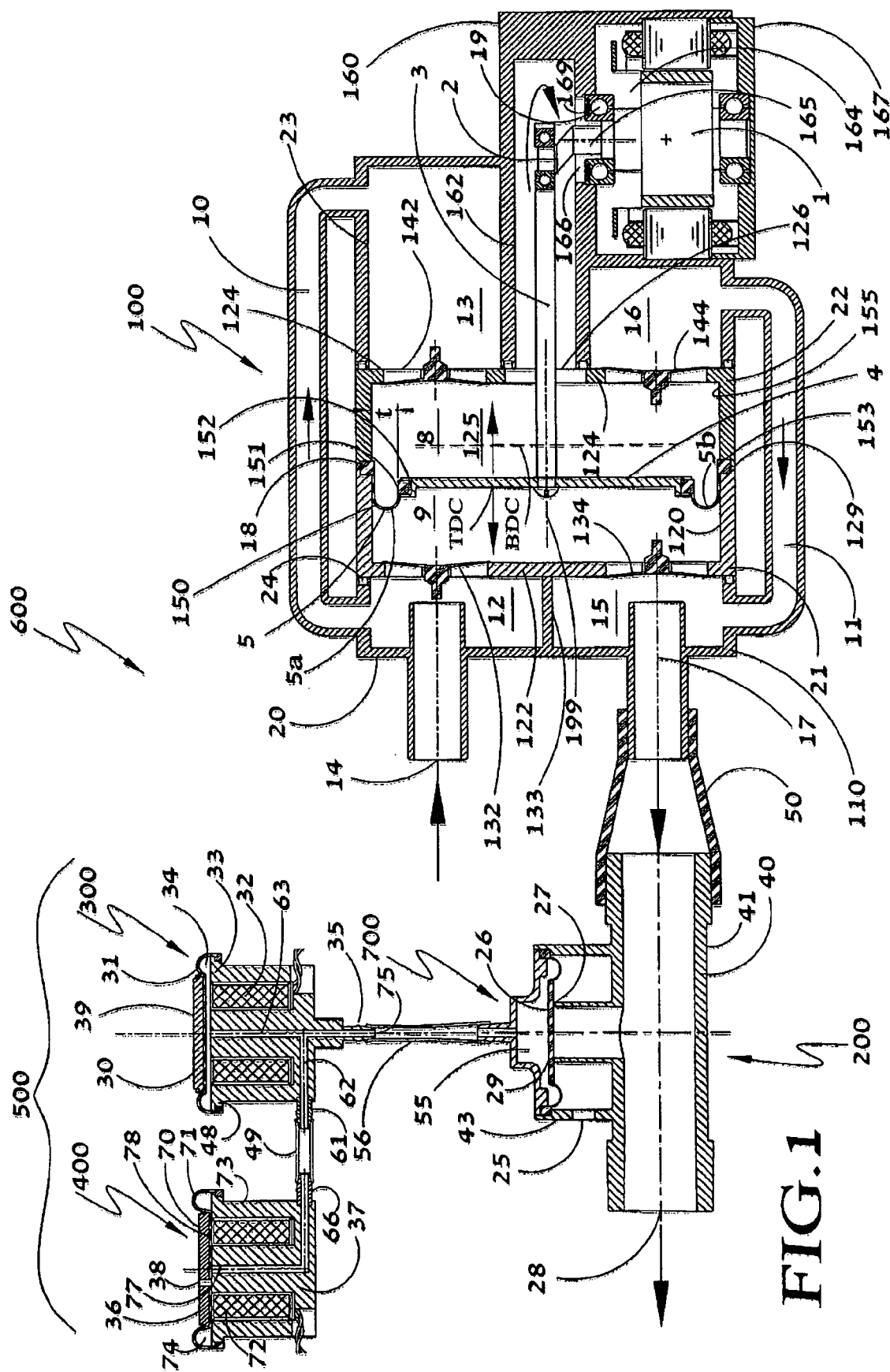
FIG. 1 schematically illustrates in cross-sectional view, a system including a pump and exhalation valve assembly according to an embodiment of the invention, in which the exhalation valve assembly is operating in inhalation mode.
Figure 2:
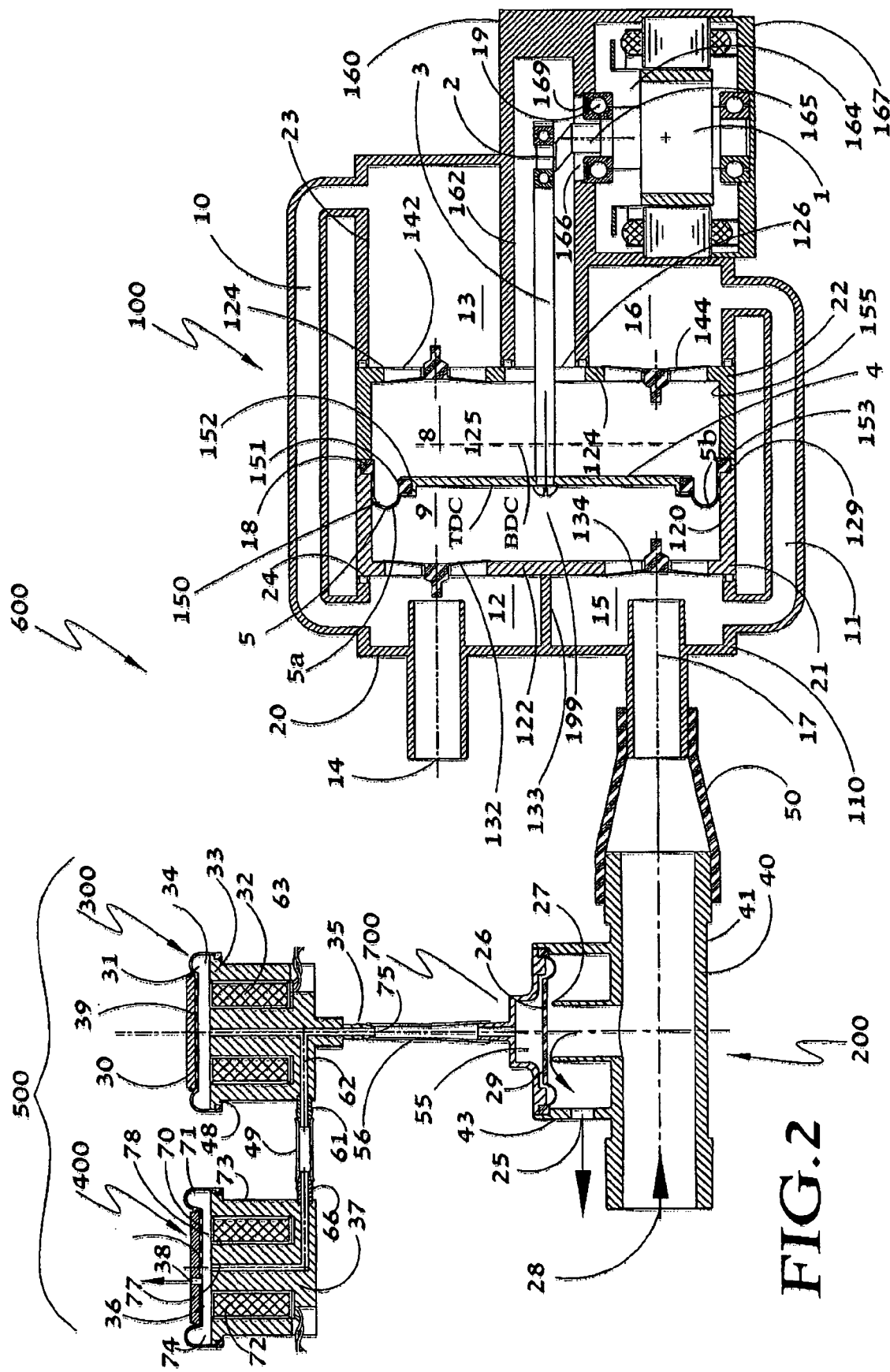
FIG. 2 schematically illustrates in cross-sectional view, the embodiment of the exhalation valve assembly of FIG. 1, in which the exhalation valve assembly is operating in exhalation mode.

Referring to FIGS. 1 and 2, a respirator apparatus according to according to an embodiment of the invention, designated with reference numeral 600, comprises pump 100 and exhalation valve assembly 200.

The pump 100 includes a housing 110 comprising a first end 20, a cylinder 120, and a second end 23. The first end 20 comprises an inlet port 14 and an outlet port 17, and the inlet port 14 may comprise a filter (not shown) for removing solid particles from the air that is inletted into the housing. In variations of this embodiment the filter may be omitted altogether, while in other variations of this embodiment a bacterial filter may be additionally or alternatively provided to filter contaminants such as bacteria, for example, and such a bacterial filter may be provided between the outlet 17 and hose 50, for example.

In use, the inlet port 14 may be in fluid communication with the atmosphere, directly or via a filter, or alternatively may be connected via a suitable coupling to an oxygen source or an oxygen enriched air source.

The outlet port 17 receives hose 50 for coupling the outlet port 17 to the exhalation valve assembly 200.

The cylinder 120 has a longitudinal axis 199, and is closed at each longitudinal end by respective partition walls 122 and 124 to define an internal chamber 125. In this embodiment, the cylinder is constructed from two parts: cylinder part 21 comprises about half of the length of the cylinder 120 plus partition wall 122, and the other cylinder part 22 comprises the remainder of the cylinder 120 plus partition wall 124. Cylinder parts 21 and 22 may each be made as integral items, or alternatively from separate components joined together in a suitable manner at join plane 129.

An anchored piston arrangement 150 includes a piston 4 and a peripheral convolution diaphragm 5 joined thereto. A piston rod 3 is attached to the piston arrangement 150 at one side of the piston 4, extending out of the chamber 125 via an opening 126 in partition wall 124. The peripheral diaphragm 5 has an inner peripheral lip or bead 152 that is sealingly received into a peripheral recess 151 provided at the edge of the piston 4, and an outer peripheral lip or bead 18 that is sealingly received at an annular recess 153 provided in the cylindrical wall 155 of the cylinder 120. In this embodiment, the annular recess 153 is located axially where the cylinder parts 21, 22 meet, at or close to plane 129.

Thus, the outer peripheral end of the piston arrangement 150 is sealingly anchored at a fixed axial position in the cylinder 120, while allowing for reciprocable operation of the remainder of the piston arrangement 150, by virtue of piston axial displacement and rolling of the diaphragm 5, as will be described below in more detail, with respect to axis 199. The piston arrangement 150 divides the internal chamber 125 into two chambers 8 and 9, which are of variable volume according to the position of the piston 4 and the diaphragm 5 therein in a reciprocation cycle thereof, and the outer peripheral end of the diaphragm 5, is sealingly anchored with respect to each pump chamber 8, 9.

Partition wall 122 is in abutment with end 20 of the housing 110, and comprises a one-way inlet valve 132 and a one-way outlet valve 134 with respect to chamber 9. Inlet valve 132 when open is in fluid communication with the inlet port 14 via inlet chamber 12, and outlet valve 134 when open is in fluid communication with the outlet port 17 via outlet chamber 15. Chambers 12 and 15 are integrally formed at end 20 of the housing 110, and are separated from one another by partition 133.

The second end 23 comprises inlet chamber 13 and outlet chamber 16, separated from one another by means of shaft chamber 162 of motor housing 160. Inlet conduit 10 connects and provides fluid communication between inlet chamber 13 and inlet chamber 12, while outlet conduit 11 connects and provides fluid communication between outlet chamber 16 and outlet chamber 15.

As will become clearer below, inlet chambers 12 and 13, and outlet chambers 15 and 16, each function as muffler chambers to reduce noise generated by the pump 100, and each of these chambers has an internal dimension that is larger than the opening(s) thereto, in particular providing at least some wall surfaces opposite the corresponding inlet valve or outlet valve of the respective pump chamber 8 or 9.

Partition wall 124 is in abutment with end 23 of the housing 110, and comprises a one-way inlet valve 142 and a one-way outlet valve 144 with respect to the chamber 8. Inlet valve 142 when open is in fluid communication with the inlet port 14 via inlet chamber 13, conduit 10 and chamber 12, and outlet valve 134 when open is in fluid communication with the outlet port 17 via chamber 16, conduit 11 and chamber 15.

Motor housing 160 is integrally formed with end 23, and comprises a motor chamber 164, in which a rotary motor 1 is accommodated, the output shaft 165 thereof passing through an aperture 166 into shaft chamber 162 via bearing 19, which comprises a suitable sealing arrangement 169 for preventing pressurized air from other parts of the pump 100, in particular from chamber 8, passing through the shaft chamber 162 and escaping through the motor chamber 164 to the atmosphere. A cap 167 closes motor chamber 164. Typically, the motor is an electric motor.

Piston rod 3 is accommodated in chamber 162, and is connected to crank 2, which is in turn mounted to the output shaft 165 also in chamber 162. No sealing is required between pump chamber 8 and chamber 162, nor between the piston shaft 3 and chamber 162 or pump chamber 8—rather, sealing of the pump chamber 8 with respect to the piston shaft 3 is effectively accomplished further downstream, via the sealing arrangement 169.

In operation, a suitable power source (not shown) is operatively connected to the motor 1 for providing power thereto, and suitable monitoring and controlling apparatus may also be connected to the pump 100, for example a transducer may be connected to outlet 17, for monitoring and controlling the output of the pump 100. Such a power source may include, for example, electrical batteries and/or an electrical mains supply.

The pump 100 operates as a dual acting pump, and is thus configured to produce two output strokes for each reciprocatory cycle of piston 4. As the motor 1 is operated to turn output shaft 165, crank 2 reciprocates the piston rod 3, inducing linear reciprocating travel along axis 199 of the piston 4 between a top dead center position (TDC) and a bottom dead center position (BDC). Concurrently, the piston 4 reciprocably drives the convolution diaphragm 5 along axis 199 with respect to chamber 9, alternately drawing in air through inlet valve 132 (via inlet port 14 and inlet chamber 12) into pump chamber 9 in an input stroke, and displacing a volume V of air through outlet valve 134 to outlet port 17 (via outlet chamber 15) in an output stroke, and, with respect to chamber 8, also alternately drawing in air through inlet valve 142 (via inlet port 14, chamber 12, inlet conduit 10 and chamber 13) into pump chamber 8 in an input stroke thereof and displacing another volume V of air through outlet valve 144 to outlet port 17 (via outlet chamber 16, outlet conduit 11, outlet chamber 15) in the output stroke thereof. Operation of chamber 8 is in reverse relationship to operation of chamber 9, and thus the input stroke of one chamber 8 occurs concurrently with the output stroke of the other chamber 9, and vive versa. In each output stroke of the respective chamber 8 or 9, the air or gas in the respective chamber becomes pressurized above the delivery pressure (e.g. above ambient) and thus the respective drawn volume V of air is delivered in a pressurized manner to the output port 17. Thus, continuous operation of the reciprocating piston arrangement 150 generates a continuous airflow, and each incremental rotation of the motor results in a corresponding incremental delivery of pressurized air via outlet 17.

The convolution diaphragm 5 is of the rolling type, and may be made from rubber or other suitable flexible materials, for example. The convolution diaphragm 5 is fitted in the cylinder 120 adopting a configuration wherein an outer peripheral part of convolution diaphragm 5 proximal to bead 18 is in abutment with a corresponding portion of the cylindrical wall close to recess 153, and an inner peripheral part of the convolution diaphragm 5 proximal to bead 152 adopts a bulging configuration with the piston 4 throughout full reciprocal translation of the piston 4, having a convex surface 5a (i.e., the surface having a generally convex cross-section) facing chamber 9 and a concave surface 5b (i.e., the surface having a generally concave cross-section) facing chamber 8. As the piston 4 travels from the TDC position to the BDC position, the outer peripheral part of the convolution diaphragm 5 unrolls and progressively adopts the bulging configuration, while the inner peripheral part of the convolution diaphragm 5 progressively adopts a generally cylindrical configuration. Thus in every reciprocation cycle, one or another part of the convolution diaphragm 5 is always bulging in the same axial direction, always in the direction towards chamber 9. It is to be noted that the diaphragm 5 may instead be configured to be always bulging in the direction of chamber 8 (rather than chamber 9), and thus even when chamber 8 is in its output stroke the diaphragm 5 does not collapse. Thus, the direction or pump chamber in which the diaphragm 5 is bulging towards is fixed during operation of the pump.

While the convolution diaphragm 5 is thus sufficiently flexible to roll over itself in both axial directions along axis 199 in each reciprocation cycle to roll the bulging part from one peripheral end to another peripheral end of the diaphragm 5, and the diaphragm 5 is at the same time configured to avoid collapsing of the bulging part of the diaphragm 5 when pressure is applied to the convex side 5a, such as during the output stroke of pump chamber 9 and the air therein is being pressurized. In this embodiment this is achieved by maintaining the cross-section of the diaphragm small, i.e., using a diaphragm having a small convolution radius and in a compact U-shape, while making the diaphragm from a relatively flexible material, for example a rubber compound, having a hardness of between about 50 and about 70 Shore A, for example. The relatively small cross-section of the diaphragm 5, as compared to the dimensions of the piston 4, together with the rigidity of the diaphragm 5, help to center the piston 4 within the cylinder 120 and thus along axis 199. While the diaphragm 5 is sufficiently flexible for rolling and unrolling in either direction along axis 199, the generally arcuate and relatively small cross-section thereof provides a resistance to collapsing immediately when subjected to a positive pressure on the convex side 5a.

In this embodiment, collapse of the diaphragm 5 is avoided completely in the outlet stroke of chamber 9, and this is facilitated by configuring the piston 4, which is substantially rigid, to take up the majority of the pressurized area of the piston arrangement 150. In particular, the convolution diameter t of the diaphragm 5 is between about 5% and about 15% of the diameter D of piston 4, wherein the convolution diameter t is taken as half the linear difference between the diameter Dcyl of cylindrical wall 155 and the diameter D of the peripheral edge of the piston 4. Thus, the diameter $D_{cyl}$ of the cylinder 120 at plane 129 is (2*t+D). This configuration confines the diaphragm 5 to a relatively narrow annular region or space at the extremity of the piston 4, and thereby applies a rigidity to the diaphragm 5 sufficient to prevent it from collapsing, and inverting so that it bulges in the opposite direction, under the positive pressure of the output stroke acting on the diaphragm 5. In operation, the piston 4 may be considered to essentially "float", in a manner of speaking, between the TDC and the BDC positions, and the diaphragm 5 thus acts as a bearing for the piston 4. Thus, unlike piston/seal arrangements which slide in a cylinder inducing some friction between the piston seal rings and the cylinder, the rolling diaphragm 5 provides almost no friction or resistance to the reciprocating movement of piston 4, while maintaining a complete seal between the two sides of the piston 4, and thus between pump chambers 8 and 9.

At least some embodiments of the present invention are characterized by providing noise reduction features for the pump. For example, in this embodiment, the pump chambers 8 and 9 each comprise a relatively large minimal volume, when the piston 4 is at the BDC or TDC position, respectively, and each such minimal volume is larger than about 50% of the volume displaced or swept by the piston 4 during translation between BDC and TDC, herein referred to as the swept volume of the piston 4. This additional minimal volume in each chamber 8, 9, while contributing to a reduction in pump efficiency, nevertheless results in a moderate pressure change in each of chambers 8 and 9 at their respective output strokes as the piston 4 reaches BDC and TDC positions, respectively, and reverses its travel direction thereat. The more moderate the pressure change, the less abruptly the corresponding inlet and outlet valves of the respective chambers open and close, thereby reducing noise levels produced by the valves. Of course, the said one-way inlet valves and outlet valves are configured for duly opening and closing taking into account these moderate pressurization levels. In alternative variations of this embodiment, the aforesaid minimal volumes of chambers 8 and 9 beyond the TDC and BDC positions may be substantially greater than about 50% the swept volume of the piston 4, and may each be for example any one of about 75%, 100%, 125%, 150% or greater than 150% of the swept volume of the piston 4.

Noise reduction is further enhanced in this embodiment by providing inlet chambers 12 and 13, and outlet chambers 15 and 16, each of which in this embodiment has an internal volume at least about 50% of the swept volume of the piston 4. In alternative variations of this embodiment the internal volume of one or both inlet chambers 12, 13 and/or one or both of the outlet chambers 15, 16, may each be greater than about 50%, for example any one of about 75%, 100%, 125%, 150% or greater than 150% of the swept volume of the piston 4. Chambers 12, 13 thus act as mufflers to prevent a significant proportion of the noise produced by the opening and closing of valves 132 and 142, from exiting via the inlet port 14, and chambers 15, 16 similarly act as mufflers to prevent a significant proportion of the noise produced by the opening and closing of valves 134 and 144, from exiting via the outlet port 17. In particular, each chamber 12, 13, 15, 16 may be designed for noise cancellation of the sound waves generated by the corresponding valves, wherein the reflected sound waves diffuse the generated sound waves.

At least some embodiments of the present invention are further characterized by constructional parameters of the piston. For example, in this embodiment, the relatively small translation of the piston 4 from TDC to BDC allows the use of a smaller diaphragm convolution than would otherwise be the case, increasing its resistance to collapsing under a positive pressure force acting on its convex surface 5a, as well as minimizing its wear. Thus, the volumetric displacement V produced by the pump 100 is accomplished by use of a piston arrangement having a relatively large surface area normal to axis 199, while having a relatively small piston translation r. Further, in this embodiment, the ratio D/r of the piston diameter D to the piston translation r is at least about 5, and optimally may be set at any suitable value between about 5 and about 10, though in alternative variations of this embodiment the ratio D/r may be greater than 10. Reducing the axial displacement r too much may require a very large piston diameter D to provide the required swept volume of the piston 4. While this increases the ratio D/r, the resulting larger size of the piston may introduce vibration problems due to the increased piston mass, as well as increase the overall size of the pump 100. On the other hand, increasing r results in increasing the stroke of the piston 4, i.e., the axial displacement between TDC and BDC, which in turn requires a longer diaphragm convolution to accommodate the increased stroke. Thus, in practice all these factors are considered for a particular design of pump 100, to arrive at the optimum value of D/r therefor.

At least some embodiments of the present invention are further characterized by constructional layout of the pump. For example, in this embodiment, the pump housing 110 is assembled from essentially four sections: the first end 20, cylinder parts 21 and 22, and the second end 23, stacked together with respect to axis 199, and each section is sealed with respect to an adjacent section via respective O-ring seals 24 disposed between each adjacent pair of sections. In this embodiment, the bead 18 also acts as a seal, and thus connection of the two cylinder parts 21, 22 does not require an additional seal. While the conduits 10 and 11 are illustrated in FIG. 1 as being separate components which are connected to the ends 20 and 23, the conduits 10, 11 may be formed within the walls of the cylinder parts 21, 22, and connect to the respective inlet and outlet chambers. Thus, stacking the first end 20, cylinder parts 21 and 22, and the second end 23, will result in the connection of both inlet chambers on the one hand, and of both outlet chambers on the other hand. This simple constructional layout may be considered as modular in form, and allows for low manufacturing costs (for example as molded components, made for example from suitable plastic materials), and for ease in assembly, disassembly and replacement of sections.

In an alternative variation of this embodiment, the piston arrangement 150 is replaced with a reciprocating piston which is slidingly sealed with respect to cylindrical wall 155 via sliding seal, for example piston rings or the like, and thus does not comprise a convolution diaphragm. Otherwise, such a pump apparatus is in all other respects substantially similar to the embodiment illustrated in FIG. 1, and may provide similar performance though at reduced efficiency with respect thereto.

Pump 100 is connected to exhalation valve assembly 200 via hose 50, which is configured for coupling the outlet port 17 to delivery tube 40 of the exhalation valve assembly 200, and which in practice may be relatively long so as to distance the pump 100 from the patient.

Exhalation valve assembly 200 comprises exhalation valve 700 and control valve assembly 500 for controlling the operation of the exhalation valve 700 in order to permit inspiration and exhalation by the patient. Control valve assembly 500 comprises a solenoid pump unit 300 and a two-way control valve 400.

The exhalation valve 700 includes delivery tube 40, which has an essentially T-shaped construction, having an inlet port 41, outlet port 28; exhalation valve discharge port 25 leading to the atmosphere; and a valve member 26 for selectively permitting fluid communication between the outlet port 28 and the exhalation port 25. The valve inlet port 41 is configured for being coupled to hose 50 and thereby to pump 100. Exhalation valve outlet port 28 is configured for connection to the patient being respirated, and delivers air (or other gas, for example oxygen or oxygen enriched air) pumped by the pump 100 to the patient via a suitable interface, such as a patient air delivery hose, or a mask or cannula (not shown), for example. Valve member 26 is in the form of a diaphragm 29 seatable on a valve seat 27 and controlled by the differential pressure between that at the inlet port 41 on one side of the diaphragm, and a control chamber 55 on the opposite side of the diaphragm 29. Control chamber 55 is connected by a tube 56 to the solenoid pump unit 300, such that the operation of the control valve assembly 500 controls the pressure within chamber 55, and thereby the operation of valve member 26.

Solenoid pump unit 300 comprises a valve housing 33, which includes a solenoid comprising a coil 32, and control member 30, which comprises an armature or clapper 39 aligned with the coil 32. The control member 30 further comprises a resilient diaphragm 31 peripherally attached to the armature 39 and to a seat 48 on the housing 33, to define a valve chamber 34 of variable volume between the control member 30 and the housing seat 48. The diaphragm 31 has a generally concave form with respect to chamber 34, and a resilience, such that the diaphragm 31 biases the armature 39 in a direction away from the seat 48, but may nevertheless allow movement of the armature 39 towards seat 48 when the solenoid pump unit 300 is actuated. In this embodiment, the solenoid pump unit 300 is configured for preventing abutting contact between the control member 30 and the housing seat 48 when the solenoid coil 32 is energized, and thus allowing for quick release when the coil is de-energized. This is accomplished by controlling the power to the solenoid coil 32 so as to generate sufficient magnetic attraction to only partially overcome the bias provided by the diaphragm 31, such that the control member 30 is closer to the housing seat 48, but still spaced therefrom. In this embodiment, the diaphragm 31 also extends below the armature 39 preventing contact between the armature 39 and the housing seat 48. Solenoid pump unit 300 further comprises an inlet port 61 connected via first passageway 62 to control port 35, which is connected via tube 56 to control chamber 55 of the exhalation valve 700. A second passageway 63 connects valve chamber 34 with the first passageway 62.

Two-way control valve 400 may comprise any suitable 2-way controllable valve capable of being selectively opened and closed, and in this embodiment has a construction similar to that of the solenoid pump unit 300, mutatis mutandis, comprising a valve housing 73 (including seat 78), a solenoid comprising a coil 72, control member 70 (comprising armature 36 and resilient diaphragm), a valve chamber 74, similar to the components disclosed for the solenoid pump unit 300, mutatis mutandis. However, in the two-way control valve 400, the armature 36 comprises an aperture 38, which provides fluid communication between the atmosphere and the valve chamber 74 when the armature 38 is spaced from the housing seat 78, but which is closed when the armature 38 is in abutting contact with the housing seat 78; and furthermore, the two-way control valve 400 comprises a passageway 77 that connects valve chamber 74 with an outlet port 66.

A conduit 49 connects the outlet port 66 with the inlet port 61.

In operation of the system 600, the exhalation valve assembly 200 operates in two modes: inhalation mode and exhalation mode.

In inhalation mode, and referring to FIG. 1 in particular, the control valve assembly 500 is controlled to provide rapid closing of valve member 26 with respect to valve seat 27, thereby ensuring that air (or other gas) pumped by pump 100 is uninterruptedly provided to the patient via delivery tube 40. To do so, a suitable control unit (not shown) controls operation of the control valve assembly 500 as follows. First, regarding control valve 400, the solenoid 72 is selectively electrically energized and the armature 36 is attracted magnetically towards the housing seat 78, according to the magnetic force generated by the current passing through coil 72. This results in the control member 70 being seated in abutting contact on seat 78, sealingly closing the aperture 38. Then, and regarding solenoid pump unit 300, the solenoid 32 is selectively electrically energized and the armature 39 is attracted magnetically towards the housing seat 48, according to the magnetic force generated by the current passing through coil 32. This results in the air trapped in chamber 34 and in air passages 75 of the control valve system 500 (the air passages 75 including passages 62, 63 and 77, conduit 56 and control chamber 55), being pressurized, increasing the pressure in the control chamber 55 to higher than that at the inlet port 41, and thus causing the valve member 26 to close. Thus, the control member 30 operates essentially as a pump, providing a pressure stroke that pressurizes the control chamber 55 and closes the valve member 26. It is alternatively possible to actuate both coils 32and 72 simultaneously if two-way control valve 400 is configured for closing much faster than solenoid pump unit 300 is able to operate.

It is to be noted that since the two-way control valve 400 is closed first, the pressure of the air trapped within the air passages 75 will be at ambient atmospheric pressure, and thus subsequent operation of the solenoid pump unit 300 will pressurize these air passages to a pressure above ambient, starting the pressurization at nominally ambient atmospheric pressure.

In exhalation mode, and referring to FIG. 2, both coils 32 and 72 are de-energized, and the resilience of the respective diaphragms 31 and 71 respectively return the respective armatures 39 and 36 to their inactive positions, spaced away from the respective housing seats 48 and 78. Accordingly, the aperture 38 depressurizes the air passages 75 by venting the same to the atmosphere, and valve member 26 is then unseated by virtue of the higher pressure of the exhalation air delivered to the delivery tube 40 from the patient, permitting the patient to exhale via outlet port 28 and exhalation port 25 leading to the atmosphere.

At least some embodiments of the present invention are characterized by providing safety enhancement features for the exhalation valve assembly. For example, in the embodiment illustrated in FIGS. 1 and 2, the control valve assembly 500 comprises two actuable components, solenoid pump unit 300 and two-way control valve 400, which are linked in series to interconnect the valve chamber 74, valve chamber 34 and control member 55 via passages 62, 63 and conduits 49, 56. During normal operation of the control valve assembly 500 both components are de-energized, and thus opened, in the exhalation mode. However, the construction of the control valve assembly 500 is such that even if one of the components has a malfunction and fails to open, having the other component in the open position will nevertheless ensure that the pressure in control chamber 55 will return to ambient atmospheric pressure, and thereby permit the patient to exhale. For example, if control valve 400 is opened while solenoid pump unit 300 remains closed, the control member 55 is directly vented to the atmosphere via conduit 56, passage 62, conduit 49, passage 77, valve chamber 74 and aperture 38. On the other hand, if solenoid pump unit 300 is opened while control valve 400 remains closed, the control member 55 is effectively depressurized to atmospheric, as the volume in the valve chamber 34 is increased and conditions in air passages 75 revert to those that prevailed prior to actuation of the solenoid pump unit 300 during the previous inhalation mode, i.e., at ambient atmospheric pressure, which also results in the valve member 26 being opened as the pressure in the control member 55 is again at atmospheric. Thus, this arrangement provides a high degree of safety and avoids a potentially hazardous situation with respect to the patient which could otherwise result if the valve member 29 remained closed during exhalation. Failure of both components 300 and 400 is statistically a much rarer event than failure of a single control valve, and the resulting redundancy can increase the reliability of the control valve assembly 500 by several fold.

In alternative variations of this embodiment, the aforesaid safety feature of the exhalation valve assembly may be omitted, and thus the exhalation valve assembly comprises only one component, similar to solenoid pump unit 300, but without the passage 62 and is thus not ventable thereby to atmosphere, and thus passage 63 provides fluid communication between the pump chamber 34 and outlet 35, and via conduit 56, to the control chamber 55. Operation of such an embodiment is based on closing the solenoid pump unit during inhalation mode to pressurize the control chamber 55, and opening the control valve during exhalation to unseat the valve member 26 from the seat 27. Such an arrangement may function in a satisfactory manner, with the possible exception of the case where there is a leak with respect to passage 63, for example in tube 56 or diaphragms 31 or valve member 26, wherein each time the valve opens the leakage is offset/restored by flow from the atmosphere.

At least some embodiments of the present invention are further characterized by constructional layout of the control valve assembly 500. For example, in the embodiment illustrated in FIGS. 1 and 2, each one of control valve 300 and control valve 400 comprises a respective control member 30, 70, having a construction including a respective armature 36, 39 that is mounted to the respective housing seat 48, 78 by means of a respective flexible, resilient diaphragm 31, 71. The diaphragms 31, 71, allow for substantially friction-free, floating movement of the respective armature 36, 39 with respect to the respective housing seat 48, 78, or at least with much reduced frictional forces as compared with other types of construction, allowing for accurate control of the pressure induced in the air passages 75 by the actuation of the solenoid pump unit 300, without hysteresis, or at least minimizing hysteresis as compared with other types of construction. This construction thus provides a control valve arrangement that produces as essentially hysteresis-free control of the exhalation valve assembly 200.

Operation of the system 600 is as follows. During patient inhalation, the exhalation valve assembly 200 is operated in inhalation mode, as described above, and the pump 100 generates and provides pressurized air to the patient, as described above, via the outlet port 28 of the exhalation valve assembly 200. During patient exhalation, the exhalation valve assembly 200 is operated in exhalation mode, as described above, and the pump 100 is stopped. Alternatively, the pump 100 may be set to operate continuously, even during the exhalation mode, such that while most of the pressurized air generated by the pump is discharged via exhalation port 25 during exhalation mode, a low pressure is still maintained in the patient's lungs (commonly referred to as "positive end exhalation pressure" or PEEP). A suitable controller (not shown) controls operation of the pump 100 and of the exhalation valve assembly 200 and synchronizes operation between the two.

In alternative embodiments of the invention, the pump 100 may alternatively be used with other types of exhalation valves known per se in the art, and the resulting system controlled in a suitable manner for enabling inhalation and exhalation of the patient.

In alternative embodiments of the invention, the exhalation valve assembly 200 may alternatively be used with other types of pumps known per se in the art, and the resulting system controlled in a suitable manner for enabling inhalation and exhalation of the patient.

Finally, it should be noted that the word "comprising" as used throughout the appended claims is to be interpreted to mean "including but not limited to".

While there has been shown and disclosed example embodiments in accordance with the invention, it will be appreciated that many changes may be made therein without departing from the spirit of the invention.

The invention claimed is:

1. Double acting respirator pump apparatus comprising:
a housing having a pump cylinder, a pump inlet port for respiratory gas supply to the pump cylinder, and a pump outlet port for delivery of pressurized respiratory gas to a patient;
the pump cylinder having opposite first and second ends, and a pump member movably mounted in said cylinder and separating said cylinder into first and second pump chambers on opposite sides of said pump member between the pump member and the first end of the cylinder and the pump member and the second end of the cylinder, respectively;
said pump member being reciprocable in opposite first and second directions in a reciprocation cycle with respect to said pump chambers to provide an outlet pumping stroke with respect to the first pump chamber in which respiratory gas is pumped from said first pump chamber to said outlet chamber and out of said outlet port and an inlet stroke with respect to the second pump chamber in which respiratory gas is drawn from said inlet chamber into said second pump chamber when said pump member moves in the first direction towards the first end of the cylinder, and an outlet pumping stroke with respect to the second pump chamber in which respiratory gas is pumped from said second pump chamber to said outlet chamber and out of said outlet port and an inlet stroke with respect to said first pump chamber in which respiratory gas is drawn from said inlet chamber into said first pump chamber when said pump member moves in the second direction towards the second end of said cylinder; wherein said inlet stroke and said outlet stroke for each pump chamber defines for the respective pump chamber a displacement volume that is displaced in the respective pump chamber by reciprocation of the pump member in one reciprocation cycle between the respective inlet stroke and the respective outlet pumping stroke, and wherein a volume of at least one said pump chamber at the end of the respective said outlet pumping stroke thereof is a first proportion of the respective said displacement volume, wherein said first proportion is not less than about 50%, and wherein said pump member comprises a piston reciprocably mounted with respect to said pump chambers via a convolution diaphragm configured to support and guide the pump member in axial reciprocating movement in said opposite first and second directions in said cylinder, the diaphragm being peripherally joined to the piston and anchored with respect to said cylinder, and wherein said diaphragm is configured for avoiding being collapsed during the outlet pumping stroke of each said pump chamber.

2. Pump apparatus according to claim 1, wherein said diaphragm is configured to have a portion thereof that bulges in a direction towards said first pump chamber and away from said second pump chamber during reciprocation of said pump member in first and second directions throughout said reciprocation cycle.

3. Pump apparatus according to claim 1, wherein said housing has an end wall spaced from one end of said pump cylinder in which said inlet and outlet ports are located, at least one inlet chamber between the end wall and said one end of said pump cylinder and connected to the pump inlet port and at least one outlet chamber between the end wall and said one end of said pump cylinder connected to the pump outlet port, said pump inlet port is in fluid communication with a first inlet valve of said first pump chamber via said at least one inlet chamber having a first volume and with a second inlet valve of said second pump chamber via said at least one outlet chamber, and wherein said pump outlet port is in fluid communication with a first outlet valve of said first pump chamber via said at least one outlet chamber having a second volume and with a second outlet valve of said second pump chamber via said at least one outlet chamber, and wherein each one of said first volume and said second volume is at least a second proportion of said displacement volume of said respective pump chamber, wherein said second proportion is not less than about 50%.

4. Pump apparatus according to claim 3, wherein said inlet chamber comprises a first inlet chamber adjacent the first end of said pump cylinder and a second inlet chamber adjacent the second end of said pump cylinder, and said outlet chamber comprises a first outlet chamber adjacent the first end of said pump cylinder and a second outlet chamber adjacent the second end of said pump cylinder, and wherein said first outlet chamber is in fluid communication with said second outlet chamber, and wherein said first inlet chamber is in fluid communication with said second inlet chamber.

5. Pump apparatus according to claim 1, wherein said diaphragm has a convolution diameter that is between about 5% and about 15% of a diameter of said piston.

6. Pump apparatus according to claim 5, wherein said diaphragm is made from a flexible material, having a hardness of between about 50 Shore A and about 70 Shore A.

7. Pump apparatus according to claim 1, wherein said piston has an axial translation in a reciprocation direction of said piston between a top dead center position corresponding to an end of an outlet pumping stroke of said first pump chamber, and a bottom dead center position corresponding to an end of an outlet pumping stroke of said second pump chamber, wherein said axial translation is between about 10% and about 20% of a diameter of said piston.

8. Pump apparatus according to claim 1, wherein said piston is driven by a motor by means of a crank and piston shaft arrangement.

9. Pump apparatus according to claim 8, wherein said crank and piston shaft arrangement are accommodated in a shaft housing in fluid communication with one said pump chamber, and wherein said motor is accommodated in a motor housing and operatively connected to said crank in a manner providing for sealing of said respective pump chamber within respect to said motor housing.

10. Pump apparatus according to claim 9, wherein said motor comprises a driveshaft operatively connected to said crank, and wherein said driveshaft is mounted with respect to said shaft housing via a bearing arrangement, and wherein said bearing arrangement comprises an integral seal for sealing said respective pump chamber with respect to said motor housing.

11. Pump apparatus according to claim 4, wherein said housing comprises a first end part including said first inlet chamber in fluid communication with said first pump chamber via said first inlet valve in the inlet stroke of said first pump chamber and said first outlet chamber in fluid communication with said first pump chamber in the outlet pumping stroke of said first pump chamber, a second end part including said second inlet chamber in fluid communication with said second pump chamber via said second inlet valve in the inlet stroke of said second pump chamber and said second outlet chamber in fluid communication with said second pump chamber via said second outlet valve in the outlet pumping stroke of said second pump chamber.

12. Pump apparatus according to claim 4, wherein said pump inlet port is in fluid communication with said inlet chamber of each said pump chamber, and wherein said pump outlet port is in fluid communication with said outlet chamber of each said pump chamber.

13. Double acting respirator pump apparatus comprising a housing defining two pump chambers and a pump member reciprocable with respect to said pump chambers and configured to provide an inlet stroke and an outlet stroke with respect to each said chamber in each reciprocation cycle of said pump member, the housing having an inlet port which communicates with each pump chamber in the inlet stroke of said pump member with respect to the respective pump chamber and an outlet port configured for connection to a respirator breathing tube via respirator exhalation system, the outlet port communicating with each pump chamber in the outlet stroke of said pump member with respect to the respective pump chamber, wherein said inlet stroke and said outlet stroke for each pump chamber defines for the respective pump chamber a displacement volume that is displaced in the respective pump chamber by reciprocation of the pump member in one reciprocation cycle between the respective inlet stroke and the respective outlet stroke, and wherein a volume of at least one said pump chamber at the end of the respective said output stroke thereof is a first proportion of the respective said displacement volume, wherein said first proportion is not less than about 50%, and wherein said pump member comprises a piston reciprocably mounted with respect to said pump chambers, wherein said piston has a axial translation in a reciprocation direction of said piston between a top dead center position corresponding to an end of an output stroke of one said pump chamber, and a bottom dead center position corresponding to an end of an output stroke of the other said pump chamber, wherein said axial translation is between about 10% and about 20% of a diameter of said piston as projected in a direction substantially orthogonal to said reciprocation direction.

14. Respirator exhalation system for facilitating exhalation of a patient connected to a respiratory apparatus, comprising:
an exhalation valve comprising a valve housing, a valve seat inside the housing, and a valve member movable between a first, closed position seated against the valve seat when the exhalation system is operating in an inhalation mode and a second, open position spaced from the valve seat when the exhalation system is operating in an exhalation mode, the valve housing defining a valve control chamber on the one side of the valve member, the valve housing having a control inlet communicating with the valve control chamber, an exhaust inlet on the opposite side of the valve member from the control chamber, and an exhalation discharge port communicating with the external atmosphere and in communication with the exhaust inlet when the valve member is in the open position; and a solenoid pump unit operatively connected to the control inlet of said exhalation valve and configured for operation as a pump and selectively generating an air pressure in said control chamber sufficient for pressurizing one side of said valve member for closing the same when said exhalation system is operating in inhalation mode.

15. Respirator system according to claim 14, wherein said pump unit comprises a pump control member and a pump housing having a seat, wherein a pumping chamber is defined between said pump control member and said seat, wherein in operation of said pump unit said pumping chamber comprises a confined volume of compressible air, and wherein said pumping chamber is in fluid communication with said control chamber of said valve member, and wherein said pump unit is configured for selectively bringing said pump control member into proximity with said housing seat to compress said volume of compressible air and thereby to generate a pump pressure for pressurizing said control chamber of said valve and urging said valve member into the closed position.

16. Respirator system according to claim 15, wherein said pump control member comprises an armature, and said pump unit further comprises an electric coil in said pump housing, and wherein energizing said coil magnetically attracts said armature to bring said pump control member into proximity with said housing seat, thereby compressing air enclosed in said pumping chamber and generating said pump pressure.

17. Respirator system according to claim 16, wherein said pump unit is configured for modulating said pump pressure by selectively variably energizing said coil.

18. Respirator system according to claim 16, wherein said armature is connected to said housing seat via a flexible resilient diaphragm, wherein said diaphragm is configured for providing substantially hysteresis-free operation of said pump unit.

19. Respirator system according to claim 18, wherein said diaphragm extends between said armature and said housing seat, preventing contact therebetween when said coil is fully energized and providing for rapid separation therebetween when said coil is not energized.

20. Respirator system according to claim 18, wherein said diaphragm is biased to space said armature away from said housing seat when said coil is not energized.

21. Respirator system according to claim 14, further comprising a two-way control valve in fluid communication with said pumping chamber and said control chamber of said valve member, and configured for selectively venting said control chamber of said valve member.

22. Respiratory apparatus comprising the respiratory pump as defined in claim 1 operatively connected to a respirator exhalation system for facilitating exhalation of a patient connected to said respiratory apparatus.

23. Respiratory apparatus comprising a respiratory pump apparatus for delivering pressurized gas to a patient connected to said respiratory apparatus, the respiratory pump apparatus being operatively connected to a respirator exhalation system as defined in claim 14.

* * * * *